United States Patent [19]

Desbois et al.

[11] Patent Number: 4,837,364

[45] Date of Patent: Jun. 6, 1989

[54] PROCESSES FOR PREPARING PENTAFLUOROETHOXY- AND PENTAFLUOROETHYLTHIOBENZENE DRIVATIVES

[75] Inventors: Michel Desbois, Rillieux La Pape; Bernard Langlois, Lyons, both of France

[73] Assignee: Rhone-Poulenc Specialites Chimiques, Courbevoie, France

[21] Appl. No.: 845,192

[22] Filed: Mar. 28, 1986

[30] Foreign Application Priority Data

Mar. 29, 1985 [FR]  France ............................. 85 04755

[51] Int. Cl.[4] ..................... C07C 148/00; C07C 41/22
[52] U.S. Cl. ................................ 568/43; 204/157.77; 204/157.78; 204/157.79; 204/157.8; 204/157.82; 204/157.88; 204/157.92; 260/544 D; 260/544 S; 260/694; 558/423; 558/425; 560/18; 560/59; 568/44; 568/52; 568/54; 568/56; 568/333; 568/588; 568/633
[58] Field of Search .................. 568/44, 54, 56, 43, 568/333, 588, 633, 52; 558/423, 425; 260/544 S, 544 D, 694; 204/157.8, 157.77, 157.79, 157.82, 157.92; 560/18, 59

[56] References Cited

U.S. PATENT DOCUMENTS

| | | | |
|---|---|---|---|
| 2,803,665 | 8/1957 | Miller et al. ...................... | 260/614 |
| 3,207,792 | 9/1965 | Buchanan et al. .................. | 568/35 |
| 3,419,595 | 12/1968 | Hansen .............................. | 558/54 |
| 4,287,125 | 9/1981 | Soula ................................. | 568/56 |
| 4,643,811 | 2/1987 | Langlois ........................... | 204/158.11 |

FOREIGN PATENT DOCUMENTS

1183096 12/1964  Fed. Rep. of Germany.
2529543  1/1984  France.
2045760 11/1980  United Kingdom.

OTHER PUBLICATIONS

A. Feiring, J. Amer. Chem. Soc., 44, No. 16 (1979), pp. 2907-2910.

*Primary Examiner*—Mary E. Ceperley
*Attorney, Agent, or Firm*—Finnegan, Henderson, Farabow, Garrett & Dunner

[57] ABSTRACT

A process for the preparation of (pentafluoroethoxy)- and (pentafluoroethylthio)benzene derivatives either from phenol, thiophenol or from halobenzene. A halobenzene is reacted with trifluoroethanol or a phenol or a thiophenol is reacted with a compound of the formula $CF_3-CH_2-O-R'$. The product is chlorinated and the chlorinated product is fluorinated in liquid hydrofluoric acid in the presence of a Lewis acid.

The compounds obtained by the process of the present invention are used as synthesis intermediates in the phytosanitary, pharmaceutical and veterinary industries, and are used in lubricants.

24 Claims, No Drawings

PROCESSES FOR PREPARING PENTAFLUOROETHOXY- AND PENTAFLUOROETHYLTHIOBENZENE DRIVATIVES

The present invention relates to a process for preparing (pentafluoroethoxy)- and (pentafluoroethylthio)-benzene compounds. More particularly, the invention relates to a process for preparing the compounds either from phenol compounds, thiophenol compounds or from halobenzenes.

From W. A. Sheppard (J. Org. Chem., 1964, 29, 1), it is known to prepare (pentafluoroethoxy)benzenes by fluorination of phenyl trifluoroacetates using sulfur tetrafluoride. Unfortunately, this method cannot be industrially exploited because neither sulfur tetrafluoride nor phenyl trifluoroacetate is industrially available.

It is also known to prepare (pentafluoroethylthio)-benzenes by the action of thiophenols on pentafluoroethyl iodide in the presence of liquid ammonia and ultraviolet radiation [V. I. Popov et al., Zh. Org. Khim.; 1977, 13 (10), 2135], or the action of thiophenates on aryl(pentafluoroethyl)-iodonium salts [L. M. Yagupolskii et al., Zh. Org. Khim.; 1980 16 (1), 232]. Both of these methods require the use of pentafluoroethyl iodide, which is costly and scarcely available on an industrial scale. The use of liquid ammonia also requires special technology.

The present invention has made it possible to overcome these disadvantages and relates to a process for preparing a (pentafluoroethoxy)- and (pentafluoroethylthio)benzene compound, which compound may contain additional substituents, and which compound may be a monocyclic, polycyclic or heterocyclic aromatic compound, comprising the steps of:

(1) either (a) reacting a halobenzene compound with trifluoroethanol in an aprotic solvent in the presence of a strong base and, optionally, in the presence of a copper salt and/or a complexing agent; or (b) reacting a phenol or thiophenol compound with a compound of the formula (I)

wherein R' denotes a substituent selected from the group consisting of trifluoroacetyl, methanesulfonyl, para-toluenesulfonyl, trichloromethanesulfonyl, chlorosulfonyl and trifluoromethanesulfonyl, in the presence of a strong alkaline base, an aprotic solvent and optionally a complexing agent to obtain a 2,2,2-trifluoroethoxy aromatic compound or a 2,2,2-trifluoroethylthio aromatic compound;

(2) chlorinating the aromatic compound obtained in step (1) using gaseous chlorine in the presence of radiation and/or phosphorus trichloride; and (3) fluorinating the product obtained in step (2) with anhydrous liquid hydrofluoric acid in the presence of a Lewis acid to obtain said (pentafluoroethyoxy)- or (pentafluoroethylthio)benzene compound.

The pentafluoroethoxybenzene and pentafluoroethylthiobenzene compounds obtained in accordance with the process of the present invention may contain more than one pentafluoroethoxy or pentafluoroethylthio group and may contain more than one aromatic ring. Additionally, other substituents, such as nitro and halogen, may be present on the aromatic ring.

According to a preferred embodiment of the present invention, a bromo- or iodobenzene is reacted in step (1)(a) with a trifluoroethanolate in the presence of copper bromide or chloride in a dipolar aprotic solvent such as dimethylformamide or N-methylpyrrolidone. The reaction is preferably carried out at a temperature ranging from about 80° to 200° C.

As defined herein, the term "halobenzene" includes benzene compounds containing substituents other than halogen. Exemplary additional compounds include —NO$_2$, —CF$_3$, p—F—C$_6$H$_4$—CO—, —COCH$_3$ and COCN.

According to a second preferred embodiment, a halobenzene, which is activated by means of an electron-withdrawing substituent such as one selected from the group consisting of nitro, cyano, ester, ketone and CF$_3$, is contacted in step (1)(a) with trifluoroethanol in the presence of a base in an aprotic solvent.

The reaction of step (1)(a) can be carried out in the presence of a complexing agent, preferably corresponding to formula (II).

in which n is an integer from 0 to 10, R$_1$, R$_2$, R$_3$ and R$_4$, which may be identical or different, each denotes hydrogen or C$_1$–C$_4$ alkyl and R$_5$ denotes C$_1$–C$_{12}$ alkyl, C$_1$–C$_{12}$ cycloalkyl, phenyl, —C$_m$H$_{2m}$C$_6$H$_5$ or C$_m$H$_{(2m+1)}$C$_6$H$_4$—, and m is an integer from 1 to 12.

Still more preferably, complexing agents of formula (II) are used in which R$_1$, R$_2$, R$_3$ and R$_4$ each denote hydrogen or methyl, R$_5$ denotes a methyl group and n equals 1.

An aprotic solvent having little or no polarity can then be employed, preferably carbon tetrachloride or one of the chlorobenzenes.

Preferably, step (1)(a) of the process of the invention involves contacting a halobenzene with trifluoroethanol in a mole ratio of trifluoroethanol to halogenated benzene of from about 0.5 to 5; and a mole ratio of trifluoroethanol to base of from about 1 to 3; and, if utilized, a mole ratio of copper salt to halogenated compound of from about 0.01 to 0.2.

When the complexing agent having formula (II) is used in step (1)(a) of the process of the present invention, the mole ratio of the compound of formula (II) to halobenzene is preferably from about 0.01 to 0.2.

When step (1) of the process of the present invention involves reacting a phenol or a thiophenol with a compound of formula (I), preferred phenols or thiophenols are of the formula R$_n$-Ar-AH in which n is 1 or 2. Preferred compounds of formula (I) include 2,2,2-trifluoroethyl para-toluenesulfonate and 2,2,2-trifluoroethyl trichloromethanesulfonate.

The reaction of step (1)(b) can be carried out in the presence of a complexing agent, preferably the complexing agent of formula (II). When a complexing agent of formula (II) is used, the reaction is preferably performed in the presence of a base selected from the group consisting of alkali metal hydroxides and carbonates, alkaline earth metal hydroxides and carbonates and sodium, and also in the presence of a solvent intermediary which solubilizes the complexing agent but is chemically inert to the complexing agent. The solvent is selected from the group consisting of aprotic solvents which are apolar or of low polarity such as chlorobenzene, ortho-dichlorobenzene, 1,2,4-trichlorobenzene and carbon tetrachloride. Trichlorobenzene is preferably used.

As defined herein, the phenol or thiophenol used in step (1)(b) of the present invention may be substituted. Exemplary substituents include halogen, nitrogen, alkoxy, and hydroxy. Additionally, the terms "phenol" and "thiophenol" include both bicyclic and monocyclic phenols and thiophenols.

When step (1) of the process of the present invention involves contacting a phenol or thiophenol with a derivative of formula (I), the mole ratio of phenol or thiophenol to the compound of formula (I) is preferably from about 0.5 to 5, more preferably from about 0.7 to 1.5, and the mole ratio of base to the phenol or thiophenol is from about 0.5 to 1.1.

When the complexing agent of formula (II) is used in step (1)(b) in the process of the present invention, the mole ratio of the derivative of formula (II) to phenol or thiophenol is preferably from about 0.01 to 0.2.

It is preferred to carry out step (2) of the process of the present invention by bringing the product obtained in step (1) of the process of the present invention into contact with gaseous chlorine in the presence of radiation, preferably radiation having wavelengths 250 to 600 nm, and optionally, in the presence of a solvent. The solvents used, such as one of the chlorobenzenes, or preferably, carbon tetrachloride, withstand chlorination and are liquid at room temperature and atmospheric pressure. When the product obtained in step (1) of the process of the present invention is liquid and the benzene ring of the product of step (1) contains at least one electron-withdrawing group, such as one selected from the group consisting of halogens, trifluoromethyl, trifluoromethoxy, trifluoromethylthio, nitro, cyano and chlorocarbonyl, the reaction of step (2) preferably occurs out without a solvent.

The reaction of step (2) preferably takes place at atmospheric pressure. However, in the case of a product obtained from step (1) in which the benzene ring contains at least one electron-withdrawing substituent, a higher pressure in step (2) is advantageous.

The reaction temperature is preferably of step (2) from about 70° to 200° C. More preferably, when the reaction is performed in the presence of a carbon tetrachloride, the reaction temperature of step (2) is from about 70° to 85° C.

Radiation used in step (2) of the process of the present invention generally can be obtained by using a discharge tube containing rare gases and/or mercury vapor.

Step (2) of the process of the present invention can also be carried out according to the teaching of German Pat. No. 1,183,096, the disclosure of which is specifically incorporated by reference herein, by means of gaseous chlorine in the presence of phosphorus trichloride and radiation at a temperature of from about 100° to 200° C.

Step (2) of the process can also be carried out by means of gaseous chlorine using only phosphorus trichloride as a catalyst at a temperature of from about 120° to 200° C.

In step (3) of the process of the present invention, the product obtained in the second stage is brought into contact with anhydrous liquid hydrofluoric acid in the presence of a Lewis acid. The Lewis acids employed in the process of the invention are preferably selected from the group consisting of $BF_3$, $SbCl_5$, $SbF_5$, $SnCl_4$, $SnF_4$, $TiCl_4$, $TiF_4$, $NbF_5$, $TaF_5$, $PF_5$, $AsF_5$, $MoF_6$ and $WF_6$. Antimony pentachloride ($SbCl_5$) or boron trifluoride ($BF_3$) is more preferably used as the Lewis acid.

The mole percent of the Lewis acid to the product obtained in step (2) is preferably from about 1 to 20%, more preferably from about 5 to 15%. The mole ratio of hydrofluoric acid to the product obtained in step (2) is from about 5 to 50, preferably, from about 10 to 30. The reaction temperature of step (3) is from about 0° to 180° C., preferably from about 80° to 150° C.

The (pentafluoroethoxy)- or (pentafluoroethylthio)-benzene derivatives are used as synthesis intermediates in the pharmaceutical, veterinary and phytosanitary industries, and are also used in lubricants (U.S. Pat. No. 4,366,168, European Pat. No. 44,808, U.S. Pat. No. 3,265,741).

The present invention will be described more completely with the aid of the following examples, which are merely representative and do not serve to limit the scope of the invention.

EXAMPLE 1

Synthesis of 4-Chloro-(2,2,2-trifluoroethoxy)benzene from 4-chloro-1-bromobenzene and trifluoroethanol.

A 1-liter four-necked round-bottomed flask equipped with a central mechanical stirrer, a thermometer pocket and a reflux condenser, was charged with 200 ml of anhydrous dimethylformamide (freshly distilled) and 135 g (1.35 mole) of anhydrous trifluoroethanol. The mixture was cooled in a bath of ice water, and 65 g of a 50% strength suspension of sodium hydride in liquid paraffin "equivalent to a total of 32.5 g (1.35 mole) of pure NaH" were added in the course of 1 hour in small portions. During this addition, the temperature was maintained at between 15 and 17° C. so as to obtain a regular evolution of hydrogen. When the addition was complete, the ice bath was removed and the temperature of the medium was allowed to rise slowly to 32° C. Evolution of hydrogen was still observed. When the temperature became stable at about 30° C., the reaction mass was heated slowly to 78° C., at which it was maintained for 1 hour until the evolution of gas ceased.

The mixture was then cooled to 25° C. and 22 g (0.10 mole) of anhydrous cupric bromide (dried for 1 hour at 150° C.) were added. The temperature rose spontaneously to 55° C., and a solution of 249 g (1.3 mole) of 4-chloro-1-bromobenzene in 300 ml of anhydrous di-methyl-formamide (freshly distilled) were added over a 30 minute period.

The black mixture obtained was heated to about 130°–135° C. and maintained there for 1 hour 45 minutes.

After cooling, the reaction mass was filtered, the precipitate washed with 200 ml of ethyl ether and then combined with the filtrate and the organic phase was poured into 500 ml of distilled water. This mixture was extracted with 3×200 ml of ether and the new ether phase was again washed with 3×100 ml of distilled water, dried over anhydrous sodium sulfate and evaporated. The evaporation residue was distilled under reduced pressure using a 20 cm column filled with Fenske rings, and 244 g of 4-chloro-(2,2,2-trifluoroethoxy)-benzene (b.p.$_{25}$ 77°–77.5° C.) were collected, representing an 89% yield.

EXAMPLES 2 TO 12

Synthesis of (2,2,2-trifluoroethoxy)benzenes by condensation of sodium trifluoroethanolate with the corresponding bromobenzenes identified in Table I in the presence of a copper salt identified in Table I.

The procedure set forth in Example 1 was followed with the exception apparent from Table I. Sodium trifluoroethanolate was prepared in situ by the action of sodium hydride on trifluoroethanol. The synthesis is described by the following formula:

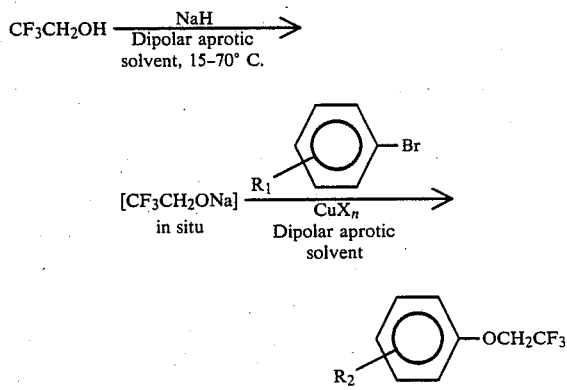

The conditions and the results are summarized in Table I.

EXAMPLE 13

Synthesis of 4-chloro-(2,2,2-trifluoroethoxy)benzene from 1,4-dichlorobenzene and trifluoroethanol.

The procedure set forth in Example 1 was used employing a reaction time of 6 hours at 120°-130° C. and the following compounds.
- 73.5 g (0.5 mole) of p-dichlorobenzene
- 53 g (0.53 mole) of $CF_3CH_2OH$
- 25.5 g (0.53 mole) of NaH, 50% strength
- 9 g (0.040 mole) of $CuBr_2$
- 200 ml of DMF A 2% yield of 4-chloro-(2,2,2-trifluoroethoxy)benzene was recovered.

EXAMPLE 14

Synthesis of (2,2,2-trifluoroethoxy)benzene from bromobenzene and isolated sodium trifluoroethylate. The sodium trifluoroethylate is obtained by the action of sodium hydroxide on trifluoroethanol.

A four-necked round-bottomed flask equipped with a central mechanical stirrer, a thermometer pocket, a dropping funnel and a short Vigreux column surmounted by a condenser with a Dean and Stark decanter for recycling the lower phase was charged with 155 g (1.55 mole) of trifluoroethanol and 100 ml of 1,1,2-trichloro-1,2,2-trifluoroethane. While the temperature was maintained at about 15°-20° C., a solution of 20 g (0.5 mole) of sodium hydroxide in the minimum amount of water was introduced slowly into the mixture. The reaction medium was brought to the reflux temperature of the azeotrope, and the distilled water was decanted as it formed. When no further decantation of the heteroazeotrope was observed, the contents of the condenser were combined with those of the reactor, and the mixture was evaporated under reduced pressure. The crude solid trifluoroethylate thereby obtained was reacted with bromobenzene (78.5 g; 0.5 mole) in dimethylformamide (500 ml) in the presence of 2 g (0.009 mole) of dry cupric bromide in the manner described in Example 1.

After 5 hours at 120° C., 26% of distilled (2,2,2-trifluoroethoxy)benzene was recovered.

EXAMPLE 15

Synthesis of 1,4-bis(2,2,2-trifluoroethoxy)benzene from 1,4-dibromobenzene using the method set forth in Example 14, and potassium trifluoroethylate, obtained by the action of potassium hydroxide on trifluoroethanol.

80 g (0.80 mole) of trifluoroethanol were treated with 23 g (0.41 mole) of solid potassium hydroxide. The water formed was entrained azeotropically using 70 ml of 1,1,2-trichloro-1,2,2-trifluoroethane. After the liberation of water ceased, 100 ml of dimethylformamide were added to the medium and the excess trifluoroethanol and the 1,1,2-trichloro-1,2,-trifluoroethane were distilled off.

The reaction proceeded as described in Example 10 adding 60 g (0.068 mole) of 1,4-dibromobenzene and 2 g (0.009 mole) of cupric bromide. After the mixture was heated for 5 hours at 100° C., a 34% yield 1,4-bis(2,2,2-trifluoro-ethoxy)benzene was recovered.

EXAMPLE 16

Synthesis of 1,4-bis(2,2,2-trifluoroethoxy)benzene by the action of 1,4-dibromobenzene, in the presence of cupric bromide, on sodium trifluoroethylate obtained by the action of sodium on trifluoroethanol.

The same apparatus was used as in Example 1. 100 g (1.00 mole) of trifluoroethanol were charged and 4.7 g of sodium metal which had been thoroughly scraped were added at 10°-15° C. in small portions. After the addition of the metal was complete, the medium was gradually heated to 50° C. and the temperature was maintained until the evolution of hydrogen ceased. 100 ml of dimethylformamide were added and the excess trifluoroethanol was distilled off. The reaction proceeded as described in Example 15, using 16 g (0.068 mole) of 1,4-dibromobenzene and 2 g (0.009 mole) of cupric bromide.

After 4½ hours at 100° C., a 75% yield of isolated 1,4-bis(2,2,2-trifluoroethoxy)benzene was recovered.

EXAMPLE 17

Preparation of methyl 2-(2,2,2-trifluoroethoxy)benzoate from trifluoroethanol and methyl 2-fluorobenzoate.

A four-necked round-bottomed flask equipped with a central mechanical stirrer, a dropping funnel, a reflux condensor and a thermometer pocket was charged with 300 ml of freshly distilled anhydrous dimethylformamide and 26.5 g of a 50% strength suspension of sodium hydride in liquid paraffin (equivalent to 0.55 moles of pure NaH).

This stirred suspension was cooled to about 10° C. in a bath of ice water, and 55 g (0.55 mole) of anhydrous trifluoroethanol were allowed to flow over a 30 minute period. During this addition, the medium was maintained at about 10°-15° C. and a regular evolution of hydrogen was observed.

After the addition was complete, the reaction mixture was heated to 50° C. and the temperature was maintained until the evolution of hydrogen ceased.

The mixture was cooled to 35° C. and 77 g (0.5 mole) of methyl 2-fluorobenzoate were allowed to flow in, which took 1 hour. The reaction was exothermic and it was necessary to apply cooling to maintain the medium at about 45° C. That temperature was maintained for 2 hours after the addition was complete. The reaction mixture was then cooled to room temperature and immersed in water and the aqueous phase was extracted with ether.

The ether phase was then evaporated and the residue obtained was distilled under reduced pressure. 81.5 g of methyl 2-(2,2,2-trifluoroethoxy)benzoate (b.p.$_{20}$ 132°–135° C.) were obtained, representing a yield of 70%.

EXAMPLES 18 TO 22

Synthesis of (2,2,2-trifluoroethoxy)benzenes by condensation of sodium trifluoroethylate with chloro- and fluorobenzenes described in Table II, activated as to aromatic nucleophlic substitution by means of electron-withdrawing groups, in anhydrous dimethyl formamide.

The same procedure was used as set forth in Example 17, with the exception apparent from Table II. The sodium trifluoroethylate was prepared in situ by reacting sodium hydride with trifluoroethanol.

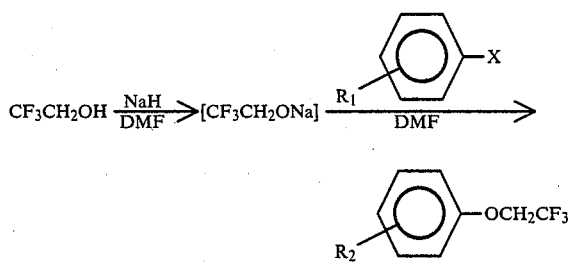

The conditions and results are summarized in Table II.

EXAMPLE 23

Synthesis of 4-(2,2,2-trifluoroethoxy)benzonitrile by condensation of trifluoroethanol with 4-fluorobenzonitrile in 1,2,4-trichlorobenzene in the presence of solid sodium hydroxide and a complexing agent.

A four-necked round-bottomed flask equipped with a central mechanical stirrer, a thermometer pocket, a dropping funnel and a reflux condenser was charged with 4.0 g (0.1 mole) of finely ground solid sodium hydroxide, 250 ml of 1,2,4-trichlorobenzene, 12.1 g (0.1 mole) of 4-fluorobenzonitrile and 1.62 g (0.005 mole) of tris(3,6-dioxaheptyl)amine of the formula N(CH$_2$—CH$_2$—O—CH$_2$—CH$_2$—O—CH$_3$)$_3$.

10 g (0.1 mole) of trifluoroethanol were allowed to flow in with stirring at room temperature, and the stirred medium was brought to 145° C. for 6 hours. The composition of the reaction mass was followed by gas chromatography.

After the reaction was complete, the reaction mixture was filtered and the precipitate rinsed with a little solvent, which was combined with the filtrate. The latter was subjected to distillation under reduced pressure using a spinning band column. 7.3 g of 4-(2,2,2-trifluoroethoxy)benzonitrile were thereby collected, representing a yield of 36%.

EXAMPLES 24 TO 29

Synthesis of (2,2,2-trifluoroethoxy)benzenes by condensation of trifluoroethanol with chloro- and fluorobenzenes (described in Table III), activated as to aromatic nucleophilic substitution, in 1,2,4-trichlorobenzene in the presence of solid sodium hydroxide and tris(3,6-dioxaheptyl)amine (TDA-1)

The same procedure as set forth in Example 23, with the exceptions apparent from Table III, was used to carry out the following reaction.

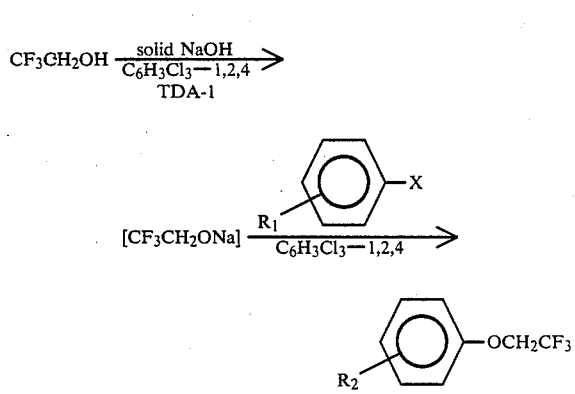

The conditions and results are recorded in Table III.

EXAMPLE 30

Synthesis of methyl 4-(2,2,2-trifluoroethoxy)benzoate by condensation of isolated sodium trifluoroethylate with methyl 4-fluorobenzoate in 1,2,4-trichlorobenzene in the presence of tris(3,6-dioxaheptyl)amine.

A four-necked round-bottomed flask equipped with a central mechanical stirrer, a thermometer pocket and a reflux condenser was charged with 50.8 g (0.508 mole) of trifluoroethanol and the mixture was cooled to 5° C. 3.76 g of a 50% strength dispersion of sodium hydride in liquid paraffin (equivalent to 0.0784 mole of pure NaH) were added in small portions in the course of 30 minutes, and the temperature was maintained at between 5° and 10° C. After addition, the temperature was allowed to rise again to about 20°–25° C. and the mixture was stirred for 1 hour until the evolution of hydrogen ceased. The unreacted trifluoroethanol was evaporated off. The solid residue obtained was then recharged in the flask with 150 g of 1,2,4-trichlorobenzene, 12.2 g (0.078 mole) of methyl 4-fluorobenzoate and 1.53 g (0.0047 mole) of tris(3,6-dioxaheptyl)amine. This mixture was heated to 140° C. and maintained for 5 hours with stirring, and was then cooled and filtered. After distillation of the filtrate, 8.83 g of methyl 4-(2,2,2-trifluoroethoxy)benzoate were recovered, representing a 48.3% yield.

EXAMPLE 31

Synthesis of 4-chloro-(2,2,2-trifluoroethoxy)benzene from 4-chlorophenol and 2,2,2-trifluoroethyl para-toluenesulfonate in N-methylpyrrolidone.

A 250-ml four-necked round-bottomed flask equipped with a central mechanical stirrer, a thermometer pocket, a dropping funnel and a reflux condenser, was charged with 80 ml of freshly distilled anhydrous N-methylpyrrolidone and 12.9 g (0.10 mole) of 4-chlorophenol. The mixture was stirred and 5 g of 50% strength suspension of sodium hydride in liquid paraffin (equivalent to 0.10 mole of pure NaH) were added in small portions. The temperature was allowed to rise spontaneously to about 50° C. and regular evolution of hydrogen was observed. When the evolution decreased, the medium was heated to about 130° C. until the formation of hydrogen ceased.

The mixture was then cooled to about 100° C. and 28 g (0.11 mole) of 2,2,2-trifluoroethyl para-toluenesulfonate were allowed to flow in over a 10 minute period. The reaction mixture was then heated to 130°–135° C. and the temperature was maintained for 4 hours 15 minutes.

After being cooled, the reaction mass was immersed in distilled water and the aqueous phase was acidified to a pH of 1.

The aqueous phase was then extracted with 3×100 ml of ethyl ether; the ether phase was washed with 100 ml of distilled water, dried and evaporated. The residue was distilled over a Vigreux column under reduced pressure. 14 g of 4-chloro-(2,2,2-trifluoroethoxy)benzene were collected, which represented a 67% yield.

EXAMPLES 32 TO 45

Synthesis of (2,2,2-trifluoroethoxy)-benzenes and (2,2,2-trifluoroethylthio)-benzenes from phenols or thiophenols and sulfonic or carboxylic acid ester of trifluoroethanol, in a dipolar aprotic solvent.

The same procedure as described in Example 31, with the exceptions apparent in Tables IV and IV (continued) was used to carry out the following reaction.

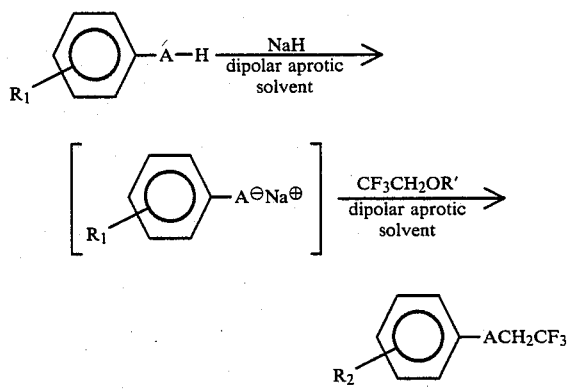

The conditions and results are recorded in Tables IV and IV (continued).

EXAMPLE 46

Synthesis of 4-chloro-(2,2,2-trifluoroethoxy)benzene from 4-chlorophenol and 2,2,2-trifluoroethyl trichloromethanesulfonate in 1,2,4-trichlorobenzene in the presence of solid sodium hydroxide and tris(3,6-dioxaheptyl)amine.

A 500-ml round-bottomed flask equipped with a mechanical stirrer, a thermometer and a small distillation column of the Vigreux type was charged with:
200 ml of 1,2,4-trichlorobenzene
4 g (0.1 mole) of finely ground sodium hydroxide
1.6 g ($5 \times 10^{-3}$ mole) of tris(3,6-dioxaheptyl)amine and
12.9 g (0.1 mole) of para-chlorophenol.

The suspension was stirred and brought to 100° C., at which temperature the water began to distill. The medium was maintained at from about 100° to 130° C. until distillation ceased.

The reaction mixture was cooled to about 30° C. and 28.2 g (0.1 mole) of 2,2,2-trifluoroethyl trichloromethanesulfonate were introduced into it.

The distillation column was replaced by a reflux condenser and the reaction medium was brought, with stirring, to 145° C. and was maintained for 4 hours.

Gas chromatography with an internal standard showed a crude yield of 4-chloro-(2,2,2-trifluoroethoxy)-benzene of 58%.

The mixture obtained after cooling was filtered and the filtrate was subjected to distillation under reduced pressure using a spinning band column.

11.6 g of 4-chloro-(2,2,2-trifluoroethoxy)benzene were collected, representing a 55% yield. (B.p.25 = 77°–77.5° C.).

EXAMPLES 47 TO 54

Synthesis of (2,2,2-trifluoroethoxy)benzenes or (2,2,2-trifluoroethylthio)benzenes from phenols or thiophenols and sulfonic or carboxylic acid esters of trifluoroethanol, in 1,2,4-trichlorobenzene in the presence of solid sodium hydroxide and tris(3,6-dioxaheptyl)amine.

These examples are summarized in detail in Table V.

EXAMPLE 55

Chlorination of 4-chloro-(2,2,2-trifluoroethoxy)benzene in carbon tetrachloride in the presence of radiation.

A cylindrical reactor having a useful capacity of two liters and equipped with a stirrer, a reflux condenser, a device for measuring temperature, a porous dipping tube for introduction of gases and a central sleeve in which a discharge lamp emitting at about 400 nm was placed, was charged with 2 liters of a solution containing 379 g (1.8 mole) of pure 4-chloro-(2,2,2-trifluoroethoxy)benzene in carbon tetrachloride.

The irradiated solution was brought to reflux under a stream of nitrogen. When refluxing was attained, the introduction of nitrogen ceased and was replaced by the introduction of gaseous chlorine (initial flow rate 520 g/h) to saturate the irradiated boiling solution with chlorine.

The photochemical chlorination lasted 3 hours, 30 minutes. Its progress was followed by gas chromatography.

When the reaction was complete, the reaction medium was maintained under reflux with irradiation and the chlorine was replaced with nitrogen until the liquid was completely outgassed. The mixture was cooled and irradiation stopped.

The carbon tetrachloride was first distilled off at atmospheric pressure, and then the 4-chloro-(1,1-dichloro-2,2,2-trifluoroethoxy)benzene was distilled off under reduced pressure (b.p.18 = 103° C.).

463 g of product were collected, representing a 92% yield.

EXAMPLE 56

Chlorination of 4-chloro-(2,2,2-trifluoroethoxy)benzene in the absence of solvent and in the presence of radiation.

The reaction was performed according to the above process, but at 150° C. in the absence of carbon tetrachloride. After 2½ hours a yield of distilled 4-chloro-(1,1-dichloro-2,2,2-trifluoroethoxy)benzene of 84% was recovered.

EXAMPLES 57 TO 70

Chlorination of (2,2,2-trifluoroethoxy)benzenes (Examples 57-67) and (2,2,2-trifluoroethylthio)benzenes (Examples 68-70) in the presence of radiation.

These examples are summarized and detailed in Table VI and Table VI (continued).

EXAMPLE 71

Chlorination of 4-chloro-(2,2,2-trifluoroethoxy)benzene in the absence of solvent and in the presence of phosphorus trichloride as catalyst.

A 100-ml reactor equipped with a bar magnet stirrer, a reflux condenser, a device for measuring temperature and a porous dipping tube for the introduction of gas was charged with 50 g of 4-chloro-(2,2,2-trifluoroethoxy)benzene and 1 g of phosphorus trichloride ($PCl_3$/$ArOCH_2CF_3$=0.036 mole/mole). The reaction medium was heated under nitrogen to 150° C., and the introduction of nitrogen was then replaced by chlorine. The temperature was maintained at between 150° and 160° C. throughout the chlorination, the progress of which was followed by gas chromatography. The chlorination was carried out for 8 hours 10 minutes. When it was complete, the introduction of chlorine ceased and, at about 150° C., the reaction mass was outgassed with nitrogen for 30 minutes. The mixture was then cooled and the desired product was distilled. A yield of 4-chloro-(1,1-dichloro-2,2,2-trifluoroethoxy)benzene of 78% was recovered.

EXAMPLE 72

Chlorination of 4-chloro-(2,2,2-trifluoroethoxy)benzene in the absence of solvent and in the presence of radiation and phosphorus trichloride.

The same procedure as set forth in Example 56 was used, but 3.6 moles % of phosphorus trichloride with respect to the organic substrate were added prior to the chlorination.

The chlorination was maintained for 4 hours 20 minutes at 150°-160° C., and a yield of 88% 4-chloro-(1,1-dichloro-2,2,2-trifluoroethoxy)benzene was recovered.

EXAMPLE 73 p-Chloro(pentafluoroethoxy)benzene

In a 250-ml stainless steel reactor stirred with a bar magnet, the following were introduced successively under an inert atmosphere ($N_2$):

3 g (0.01 mole) of anhydrous $SbCl_5$
28 g (0.1 mole) of p-chloro-(1,1-dichloro-2,2,2-trifluoroethoxy)benzene and
25 g (1.25 mole) of anhydrous HF.

The reaction mixture was brought, with stirring, to 120° C. for 3 hours 15 min. The pressure increased to 26 bars. After the reaction, the reactor was cooled to about 0° C. and the pressure released (the hydrochloric acid is allowed to escape). The reaction mixture obtained was allowed to flow onto 85 g of crushed ice. After extraction three times with 100 ml of $CH_2Cl_2$, washing of the organic phases with deionized water (100 ml) and filtration, approximately 24 g of p-chloro(pentafluoroethoxy)benzene was measured by infrared assay, which is equivalent to an analytical yield of approximately 97.5%. The absence of the starting compound was noted by means of gas chromatography.

After evaporation of the solvent, 17.2 g of para-chloro(pentafluoroethoxy)benzene were recovered (yield: 70%).

Comparative experiment

The procedure as set forth in Example 73 was used, but $SbCl_5$ was eliminated.

After 3 hours reaction, the starting material was completely recovered and no trace of p-chloro(pentafluoroethoxy)benzene was obtained.

EXAMPLE 74 p-Nitro(pentafluoroethylthio)benzene

The procedure set forth in Example 73, was employed with the following conditions and compounds:

5 g (0.017 mole) of p-nitro(1,1-dichloro-2,2,2-trifluoroethylthio)benzene;
10 g (0.5 mole) of anhydrous HF;
0.8 g (0.0027 mole) $SbCl_5$;
temperature: 100° C.; and
time: 5 hours.

Analysis by gas chromatography (standardization to 100) and mass spectrometry showed the presence of 50% of p-nitro(pentafluoroethylthio)benzene.

EXAMPLE 75

(Pentafluoroethoxy)benzene

The procedure set forth in Example 73 was employed with the following conditions and compounds.

10 g (0.4 mole) of (1,1-dichloro-2,2,2-trifluoroethoxy)benzene;
20 g (1 mole) of anhydrous HF;
0.6 g (0.002 mole) of $SbCl_5$;
temperature: 130° C.; and
time: 4 hours.

Analysis by gas chromatography (standardization to 100) and mass spectrometry showed the presence of 76% of (pentafluoroethoxy)benzene.

EXAMPLE 76 m-Chloro(pentafluoroethylthio)benzene

The same procedure as set forth in Example 73 was employed with the following conditions and compounds:

3 g (0.01 mole) of m-chloro(1,1-dichloro-2,2,2-trifluoroethylthio)benzene;
10 g (0.5 mole) of anhydrous HF;
0.3 g (0.001 mole) of $SbCl_5$;
temperature: 150° C.; and
time: 6 hours.

Analysis by gas chromatography (standardization to 100) and mass spectrometry showed the presence of 22% of m-chloro(pentafluoroethylthio)benzene.

EXAMPLE 77 p-Chloro(pentafluoroethoxy)benzene

The same procedure as set forth in Example 73 was employed with the following conditions and compounds:
- 42 g (0.15 mole) p-chloro-(1,1-dichloro-2,2,2-trifluoroethoxy)benzene;
- 50 g (2.5 mole) of anhydrous HF;
- 10 bars at 20° C. of $BF_3$;
- temperature: 100° C.; and
- time: 3 hours 45 minutes.

Analysis by gas chromatography (standardization to 100) and mass spectrometry showed the presence of 39.5% of p-chloro(pentafluoroethoxy)benzene.

EXAMPLE 78 p-Chloro(pentafluoroethoxy)benzene

The same procedure as set forth in Example 73 was employed with the following conditions and compounds:
- 42 g (0.15 mole) of p-chloro-(1,1-dichloro-2,2,2-trifluoroethoxy)benzene;
- 50 g (2.5 mole) of anhydrous HF;
- 5.8 g (0.022 mole) of $SnCl_4$;
- temperature: 15° C.; and
- time: 6 hours.

Analysis by gas chromatrography (standardization to 100) and mass spectrometry showed the presence of 38% of p-chloro(pentafluoroethoxy)benzene.

EXAMPLE 79 p-Chloro(pentafluoroethoxy)benzene

The same procedure as set forth in Example 73 was followed with the following conditions and compounds:
- 10.5 g (0.04 mole) of p-chloro-(1,1-dichloro-2,2,2-trifluoroethoxy)benzene;
- 40 g (2 moles) of anhydrous HF;
- 1 g (0.005 mole) of $TiCl_4$;
- temperature: 150° C.; and
- time: 22 hours.

Analysis by gas chromatography (standardization to 100) and mass spectrometry showed the presence of 18% of p-chloro(pentafluoroethoxy)benzene.

EXAMPLE 80

Synthesis of 1,4-bis(2,2,2-trifluoroethoxy)benzene by the action of 1,4-dibromobenzene, in the presence of cupric bromide, on sodium trifluoroethylate obtained by the action of sodamide on trifluoroethanol.

The same apparatus was used as in Example 1 100 ml of toluene were charged by 0.5 mole of sodamide. One mole of trifluoroethanol was allowed to flow in slowly.

The temperature gradually increased to 30° C. After ammonia ceased to be evolved, the toluene and excess trifluoroethanol were evaporated off. 50 ml of DMF were added, followed by 2 g of cupric bromide. 16 g (0.067 mole) of 1,4-dibromobenzene dissolved in 50 ml of DMF were allowed to flow in. The reaction was continued for 3 hours at 100° C. After hydrolysis of the reaction mixture with aqueous HCl, followed by filtration, 13 g of 1,4-bis(2,2,2-trifluoroethoxy)benzene were recovered, representing a 70% yield.

TABLE I

| No | $R_1$ | Solvent | $CH_3CH_2OH$ / NaOH moles/moles | NaH / Ar—Br moles/moles | $CuX_n$ | $CuX_n$ / Ar—Br moles/moles | T° C. | Time h | $R_2$ | Yld. |
|---|---|---|---|---|---|---|---|---|---|---|
| 2 | 4-Cl | DMF | 1 | 1.04 | $CuBr_2$ | 0.038 | 130–140° C. | 3 h | 4-Cl | 64% |
| 3 | 4-Cl | DMF | 1.05 | 1 | $CuBr_2$ | 0.025 | 120° C. | 31 h | 4-Cl | 74% |
| 4 | H | DMF | 1 | 1.05 | $CuBr_2$ | 0.078 | 120–125° C. | 3 h 40 min | H | 87% |
| 5 | H | DMF | 1.05 | 0.90 | $CuBr_2$ | 0.030 | 120° C. | 9 h | H | 68% |
| 6 | H | DMF | 1 | 0.5 | $CuBr_2$ | 0.011 | 120° C. | 5 h | H | 55.5% |
| 7 | H | DMF | 1.8 | 0.53 | $CuBr_2$ | 0.020 | 120° C. | 5 h | H | 56% |
| 8 | H | NMP | 1 | 0.91 | $CuBr_2$ | 0.020 | 120° C. | 5 h | H | 38% |
| 9 | 4-Br | DMF | 1 | 2.7 | $CuBr_2$ | 0.179 | 130–135° C. | 4 h 15 min | 4-Br / 4-$CF_3CH_2O$ | 28% / 41% |
| 10 | 4-Br | DMF | 1.4 | 3 | $CuBr_2$ | 0.074 | 100° C. | 0 h 30 min | 4-$CF_3CH_2O$ | 97% |
| 11 | 4-Br | DMF | 1.4 | 3 | CuBr | 0.032 | 100° C. | 2 h | 4-$CF_3CH_2O$ | 98% |
| 12 | 4-Br | DMF | 1.4 | 3 | CuCl | 0.074 | 100° C. | 2 h | 4-$CF_3CH_2O$ | 92% |

DMF = N,N—diethylformamide
HMP = N—methylpyrrolidone

TABLE II

| No | $R_1$ | X | $CF_3CH_2OH$ / NaH (moles/moles) | NaH / ArX (moles/moles) | T° C. | Time h | $R_2$ | Yld. |
|---|---|---|---|---|---|---|---|---|
| 18 | 4-$NO_2$ | F | 1 | 1.06 | 45° C. | 1 h | 4-$NO_2$ | 99% |
| 19 | 2-$NO_2$ | F | 1 | 1.06 | 45° C. | 1 h | 2-$NO_2$ | 92% |
| 20 | 4-$CF_3$ | F | 1 | 1.05 | 75° C. | 2 h | 4-$CF_3$ | 81% |
| 21 | 4-$CF_3$ | Cl | 1 | 1.1 | 140° C. | 8 h 30 min | 4-$CF_3$ | 1% |
| 22 | 4-(p-F—$C_6H_4$—CO) | F | 1 | 2.2 | 50° C. | 2 h | 4-(p-$CF_3CH_2O$—$C_6H_4$—CO) | 55% |

TABLE III

| No | $R_1$ | X | $CF_3CH_2OH$ / NaH (moles/moles) | NaOH / ArX (moles/moles) | TDA-1 / ArX (moles/moles) | T° C. | Time h | $R_2$ | Yld % |
|---|---|---|---|---|---|---|---|---|---|
| 24 | 4-$NO_2$ | F | 1 | 1 | 0 05 | 147° C. | 4 h | 4-$NO_2$ | 82 |

TABLE III-continued

| No | $R_1$ | X | $\dfrac{CF_3CH_2OH}{NaH}$ (moles/moles) | $\dfrac{NaOH}{ArX}$ (moles/moles) | $\dfrac{TDA\text{-}1}{ArX}$ (moles/moles) | T° C. | Time h | $R_2$ | Yld % |
|---|---|---|---|---|---|---|---|---|---|
| 25 | 4-$NO_2$ | F | 1 | 1 | 0.05 | 100° C. | 6 h | 4-$NO_2$ | 70 |
| 26 | 4-$NO_2$ | Cl | 1 | 1 | 0.05 | 130° C. | 4 h | 4-$NO_2$ | 42 |
| 27 | 2-$NO_2$ | Cl | 1 | 1 | 0.05 | 140° C. | 7 h | 2-$NO_2$ | 34 |
| 28 | 4-$CF_3$ | F | 1 | 1 | 0.10 | 145° C. | 26 h | 4-$CF_3$ | 44.5 |
| 29 | 4-(p-F—$C_6H_4$—CO) | F | 1 | 2 | 0.12 | 135–170° C. | 10 h | 4-(p-F—$C_6H_4$—CO) | 47 |
|    |                    |   |   |   |      |             |      | 4-(p-$CF_3CH_2O$—$C_6H_4$—CO) | 25 |

TDA-1 = tris(3,6-dioxaheptyl)amine

TABLE IV

| No | $R_1$ | A | $\dfrac{Ar\text{—}AH}{NaH}$ moles/moles | $\dfrac{CF_3CH_2OR'}{Ar\text{—}AH}$ moles/moles | Solvent | T° C. | Time | R' | $R_2$ | Yld. |
|---|---|---|---|---|---|---|---|---|---|---|
| 32 | 4-Cl | O | 1 | 1.2 | HMPT | 140° C. | 6 h | $CH_3SO_2$ | 4-Cl | 28% |
| 33 | 4-Cl | O | 1 | 1.2 | HMPT | 140° C. | 24 h | $CH_3SO_2$ | 4-Cl | 38% |
| 34 | 4-Cl | O | 1 | 1.2 | HMP | 140° C. | 24 h | $CH_3SO_2$ | 4-Cl | 21% |
| 35 | 4-Cl | O | 1 | 1.05 | HMPT | 120° C. + 140° C. | 2 h 5 h | $CF_3CO$ | 4-Cl | 38% |
| 36 | 4-Cl | O | 1 | 1.08 | HMPT | 120° C. | 2 h 30 min | $CCl_3SO_2$ | 4-Cl | 66% |
| 37 | 4-Cl | O | 1 | 1.05 | HMPT | 130° C. | 0 h 15 min | TsO | 4-Cl | 75% |
| 38 | 4-Cl | O | 1 | 1.1 | NMP | 130–140° C. | 6 h | $ClSO_2$ | 4-Cl | 25% |
| 39 | N | O | 1 | 1.05 | NMP + sulfolane (150:100) | 130–140° C. | 3 h | TsO | N | 72% |
| 40 | 4-$CH_3O$ | O | 1 | 1.1 | NMP | 135° C. | 3 h | TsO | 4-$CH_3O$ | 75% |
| 41 | H | S | 1 | 1.1 | NMP | 130–140° C. | 4 h | $CH_3SO_2$ | N | 64% |
| 42 | 3-Cl | S | 1 | 1.06 | NMP | 80° C. | 4 h | $CH_3SO_2$ | 4-Cl | 72% |
| 43 | 4-$NO_2$ | S | 1 | 1 | NMP | 80° C. | 4 h | TsO | 4-$NO_2$ | 58% |
| 44 |  | | 1 | 1.1 | NMP | 140–150° C. | 3 h | TsO | 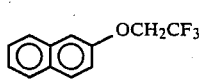 | |
| 45 | 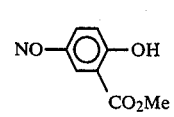 | | 0.5 | 3 | HMPT | 140° C. | 6 h 30 min | $CCl_3SO_2$ | 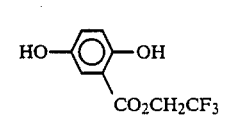 | 35% |
|    |                      | |     |   |      |         |             |             | 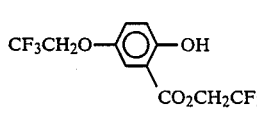 | 4% |
|    |                      | |     |   |      |         |             |             | 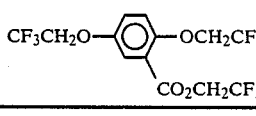 | 7% |

NMP = N—methylpyrrolidone
HMPT = Hexamethylphosphorotriamide
TsO = p-toluenesulfonyl

TABLE V

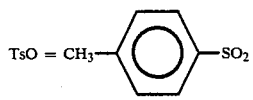

$$\text{R—Ar—A—H} \xrightarrow[\text{TDA-1/solvent/100° C.}]{\text{Solid NaOH}}$$

$$[\text{R—Ar—A}^\ominus\text{Na}^\oplus] \xrightarrow[\text{TDA-1/solvent}]{\text{CF}_3\text{CH}_2\text{OR'}}$$

$$\text{R—Ar—A—CH}_2\text{CF}_3 + \text{R'O}^\ominus\text{Na}^\oplus$$

| Experiment | R | A | Solvent | R' | Ar—A—N / CF₃CH₂OR' mole/mole | NaOH / Ar—AN mole/mole | TDA-1 / Ar—A—N moles % |
|---|---|---|---|---|---|---|---|
| 47 | H | O | TCB | TsO | 1 | 1 | 1 |
| 48 | 4-CH₃ | O | TCB | CCl₃SO₂ | 0.7 | 1 | 4 |
| 49 | 4-CH₃O | O | TCB | CH₃SO₂ | 1 | 1 | 5 |
| 50 | 2-Cl | O | TCB | CCl₃SO₂ | 1 | 1 | 5 |
| 51 | 4-Cl | O | TCB | CCl₃SO₂ | 1.2 | 0.85 | 5 |
| 52 | 4-Cl | O | TCB | TsO | 1 | 1 | 5 |
| 53 | H | S | TCB | CF₃CO | 1 | 1 | 7.6 |
| 54 | 2-OH—C₁₀H₇ | | TCB | TsO | 1 | 1 | 15 |

| Experiment | [Ar—A—N] moles/l | T° C. | Time (h) | Yld. Ar—A—CH₂CF₃ % |
|---|---|---|---|---|
| 47 | 0.4 | 170° C. | 6 | 31% crude / 21% distilled |
| 48 | 0.5 | 145° C. | 4 | 59% distilled |
| 49 | 0.33 | 140° C. | 6 | 21% crude |
| 50 | 0.5 | 145° C. | 4 | 61% distilled |
| 51 | 0.5 | 145° C. | 4 | 58% crude / 55% distilled |
| 52 | 0.5 | 150° C. + 186° C. | 6 | 27% crude |
| | | | 6 | 57% crude |
| | | 186° C. | 2 | 70% crude |
| 53 | 0.7 | 120–140° C. | 12 | 34% distilled |
| 54 | 0.5 | 140° C. + 160° C. | 12 + 6 | 20% crystallized |

TCB = 1,2,4-trichlorobenzene

TsO = CH₃—C₆H₄—SO₂

TDA-1 = N(CH₂—CH₂—O—CH₂—CH₂—O—CH₃)₃

TABLE VI

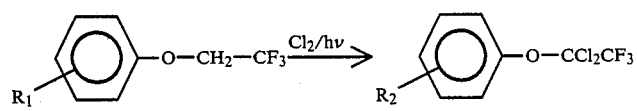

$$\text{R}_1\text{—Ar—O—CH}_2\text{—CF}_3 \xrightarrow{\text{Cl}_2/h\nu} \text{R}_2\text{—Ar—O—CCl}_2\text{CF}_3$$

| Experiment | R₁ | Solvent | [Ar—O—CH₂CF₃] | T° C. | Time | R₂ | Yld. distilled |
|---|---|---|---|---|---|---|---|
| 57 | 2-Cl | none | — | 150 | 4 h | 2-Cl | 75% |
| 58 | H | CCl₄ | 2 moles/l | 78–81 | 24 h | N | 61% |
| 59 | 4-CH₃ | TCB | 1.14 moles/l | 115 | 9 h | 4-CCl₃ | 45% |
| 60 | 4-CH₃O | CCl₄ | 1 mole/l | 78–80 | 8 h | 4-CCl₃O | 44% |
| 61 | CF₃CH₂—O-4 | CCl₄ | 5.0 moles/l | 78–80 | 6 h | 4-CF₃—CCl₂—O | 58% |
| 62 | 4-CF₃ | none | — | 120–130 | 5 h | 4-CF₃ | 73% |
| 63 | 4-CN | CCl₄ | 1 mole/l | 80 | 5 h | 4-CN | 73% |
| 64 | 4-CH₃CO₂ | ODCR | 3 moles/l | 160–170 | 12 h | 4-ClCO | 85% |
| 65 | 2-CH₃CO₂ | ODCR | 3 moles/l | 160–170 | 16 h | 2-ClCO | 65% |
| 66 | 4-(p-CF₃CH₂OC₆H₅₄CO) | CCl₄ | 0.5 mole/l | 78–80 | 20 h | 4-(p-CF₃—CCl₂—OC₆H₄CO) | 54% |
| 67 | 2-CF₃CH₂O—C₁₀H₇ | CCl₄ | 1 mole/l | 80 | 20 h | 2-CF₃CCl₂O—C₁₀H₇ | 57% |

TABLE VI-continued

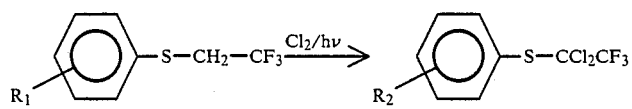

| Experiment | $R_1$ | Solvent | [Ar—S—CH$_2$CF$_3$] | T° C. | Time | $R_2$ | Yld. distilled |
|---|---|---|---|---|---|---|---|
| 68 | H | CCl$_4$ | 1 mole/l | 78-80° C. | 20 h | H | 61% |
| 69 | 3-Cl | CCl$_4$ | 1 mole/l | 78-80° C. | 19 h | 3-Cl | 56% |
| 70 | 4-NO$_2$ | CCl$_4$ | 1 mole/l | 78-80° C. | 23 h 30 | 4-NO$_2$ | 90% |

TCB = 1,2,4-trichlorobenzene
ODCB = ortho-dichlorobenzene
C$_{10}$H$_7$ = naphthyl

What is claimed is:

1. A process for preparing a pentafluoroethoxy- or pentafluoroethylthio monocyclic or condensed polycyclic aromatic compound, wherein said compound either has no further substituent or has further substituents, comprising the steps of:
   (1) either (a) reacting a haloaromatic compound with trifluoroethanol in an aprotic solvent in the presence of a strong base, or (b) reacting a phenol or thiophenol compound with a compound of the formula (I)

wherein R' denotes a substituent selected from the group consisting of trifluoroacetyl, methanesulfonyl, para-toluenesulfonyl, trichloromethane sulfonyl, chlorosulfonyl and trifluoromethane sulfonyl, in the presence of a strong alkaline base, and an aprotic solvent to obtain a 2,2,2-trifluoroethoxyaromatic compound or a 2,2,2-trifluoroethylthio aromatic compound;
   (2) chlorinating said aromatic compound obtained in step (1) using gaseous chlorine in the presence of one or more of radiation and phosphorus trichloride to obtain a 1,1-dichloro-2,2,2-trifluoroethoxy aromatic compound or a 1,1-dichloro-2,2,2-trifluoroethylthio aromatic compound; and
   (3) fluorinating said aromatic compound obtained in step (2) in anhydrous liquid hydrofluoric acid in the presence of a Lewis acid to obtain said pentafluoroethoxy- or pentafluoroethylthio aromatic compound.

2. The process of claim 1, wherein in step (1)(a) said haloaromatic compound is reacted with trifluoroethanol in an aprotic solvent in the presence of a strong base and one or more of a copper salt and a complexing agent.

3. The process of claim 1, wherein in step (1)(b), said phenol or thiophenol compound is reacted with said compound of formula (I) in the presence of a strong alkaline base and an aprotic solvent and a complexing agent.

4. The process of claim 1, wherein, during step (1)(a), said trifluoroethanol is reacted with said strong base to form a trifluoroethanolate and a bromo- or iodobenzene is reacted with said trifluoroethanolate in the presence of copper bromide or chloride in solution in a dipolar aprotic solvent.

5. The process of claim 4, wherein the mole ratio of said trifluoroethanol to haloaromatic compound is from about 0.5:1 to 5:1.

6. The process of claim 1, wherein the compound of formula (I) is selected from the group consisting of 2,2,2-trifluoroethyl para-toluenesulfonate and 2,2,2-trifluoroethyl trichloromethanesulfonate.

7. The process of claim 1, wherein the mole ratio of said phenol compound or said thiophenol compound to said compound of formula (I) is from about 0.5:1 to 5:1.

8. The process of claim 7, wherein the mole ratio of said phenol compound or said thiophenol compound to said compound of formula (I) is from about 0.7:1 to 1.5:1.

9. The process of claim 1, wherein said base is selected from the group consisting of sodium hydride, potassium hydroxide, sodium hydroxide and sodium.

10. The process of claim 2, wherein said complexing agent has the formula (II)

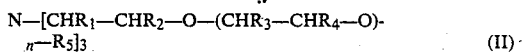

wherein n is an integer from 0 to 10, $R_1$, $R_2$, $R_3$ and $R_4$, which may be identical or different, each denotes hydrogen or a $C_1$-$C_4$ alkyl, $R_5$ denotes $C_1$-$C_{12}$ alkyl, $C_1$-$C_{12}$ cycloalkyl, phenyl, a group of the formula —$C_mH_{2m}C_6H_5$ or a group of the formula $C_mH_{(2m+1)}C_6H_4$—, m being between 1 and 12.

11. The process of claim 3 wherein said complexing agent has the formula (II)

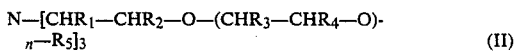

wherein n is an integer from 0 to 10, $R_1$, $R_2$, $R_3$ and $R_4$, which may be identical or different each denotes hydrogen or a $C_1$-$C_4$ alkyl, $R_5$ denotes $C_1$-$C_{12}$ alkyl, $C_1$-$C_{12}$ cycloalkyl, phenyl, a group of the formula —$C_mH_{2m}C_6H5$ or a group of the formula $C_mH_{(2m+1)}C_6H_4$—, m being between 1 and 12.

12. The process of claim 11, wherein the mole ratio of the compound of formula (II) to the phenol or thiophenol compound is from about 0.01:1 to 0.2:1.

13. The process of claim 1, wherein, during step (2), said compound obtained in step (1) is reacted with gaseous chlorine in the presence of radiation.

14. The process of claim 11, wherein, during step (2), a solvent is added which is selected from the group consisting of carbon tetrachloride and chlorobenzenes.

15. The process of claim 14, wherein said solvent is carbon tetrachloride.

16. The process of claim 1, wherein said chlorination step (2) is carried out at a reaction temperature ranging from about 70° to 200° C.

17. The process of claim 16, wherein said reaction temperature is from about 70° to 85° C.

18. The process of claim 1, wherein said Lewis acid is selected from the group consisting of antimony pentachloride and boron trifluoride.

19. The process of claim 1, wherein the mole percent of said Lewis acid to said compound obtained in step (2) is from about 1 to 20%.

20. The process of claim 18, wherein the mole percent of said Lewis acid to said compound obtained in step (2) is from about 1 to 20%.

21. The process of claim 20, wherein said mole percent is from about 5 to 15%.

22. The process of claim 1, wherein the mole ratio of the hydrofluoric acid to the compound obtained in step (2) is from abbut 5:1 to 50:1.

23. The process of claim 22, wherein said mole ratio is from about 10:1 to 30:1.

24. The process of claim 10, wherein the mole ratio of the compound of formula (II) to the haloaromatic compound is from about 0.01:1 to 0.2:1.

* * * * *

UNITED STATES PATENT AND TRADEMARK OFFICE
CERTIFICATE OF CORRECTION

PATENT NO. : 4,837,364

DATED : June 6, 1989

INVENTOR(S) : Michel Desbois et al.

It is certified that error appears in the above-identified patent and that said Letters Patent is hereby corrected as shown below:

In the title, change "DRIVATIVES" to --DERIVATIVES--.

Signed and Sealed this

Sixteenth Day of October, 1990

Attest:

HARRY F. MANBECK, JR.

*Attesting Officer*  *Commissioner of Patents and Trademarks*